United States Patent [19]
Antonson et al.

[11] Patent Number: 5,816,810
[45] Date of Patent: Oct. 6, 1998

[54] METHOD FOR PRODUCING AN ELONGATE SUPPORTING PART IN A REPLACEMENT CONSTRUCTION, AND SUCH A SUPPORTING PART MANUFACTURED USING THIS METHOD

[75] Inventors: Izidor Antonson, Partille; Lennart Carlsson, Molndal, both of Sweden

[73] Assignee: Nobel Biocare AB, Gothenburg, Sweden

[21] Appl. No.: 602,768

[22] PCT Filed: Jul. 3, 1995

[86] PCT No.: PCT/SE95/00823

§ 371 Date: Jun. 3, 1996

§ 102(e) Date: Jun. 3, 1996

[87] PCT Pub. No.: WO96/01083

PCT Pub. Date: Jan. 18, 1996

[30] Foreign Application Priority Data

Jul. 4, 1994 [SE] Sweden .................................. 9402351

[51] Int. Cl.[6] .......................................................... A61C 8/00
[52] U.S. Cl. ............................................. 433/173; 433/172
[58] Field of Search .................................. 433/172, 173, 433/174, 175, 176, 201.1

[56] References Cited

U.S. PATENT DOCUMENTS

| | | | |
|---|---|---|---|
| 4,931,016 | 6/1990 | Sillard | 433/172 |
| 5,057,017 | 10/1991 | Sillard | 433/172 |
| 5,080,671 | 1/1992 | Oron et al. | 623/16 |
| 5,246,368 | 9/1993 | Sillard | 433/172 X |
| 5,440,496 | 8/1995 | Andersson et al. | |
| 5,503,557 | 4/1996 | Sillard | 433/172 |
| 5,588,837 | 12/1996 | Rubeling et al. | 433/172 |

FOREIGN PATENT DOCUMENTS 2081588  10/1992  Canada .

*Primary Examiner*—Nicholas D. Lucchesi
*Attorney, Agent, or Firm*—Pollock, Vande Sande & Priddy

[57] ABSTRACT

An elongate supporting part in a replacement construction and a method of production thereof, the replacement construction is intended to be secured in the human body in implants with unique longitudinal courses by using at least one working model in which the longitudinal courses and connection surfaces of the implants are represented by representation members. The method comprising the steps of generating an electrical representation of the outer shape of the working model and providing this information to computer equipment. The computer equipment performs calculations in order to establish an outer shape for the supporting part and generates machining information based on this outer shape which represents the shape of the supporting part. This information is provided to a machining device which machines a blank and an electro erosion tool is created by providing electrodes in a working model at positions of the representation members. The electrodes are arranged in the same longitudinal direction as the representation members. The electro erosion tool is used to create a recess in the blank for contact members whereby the blank can be anchored on the implants. The recess and the contact members have a longitudinal axis which coincide with the axis of the implants.

11 Claims, 4 Drawing Sheets

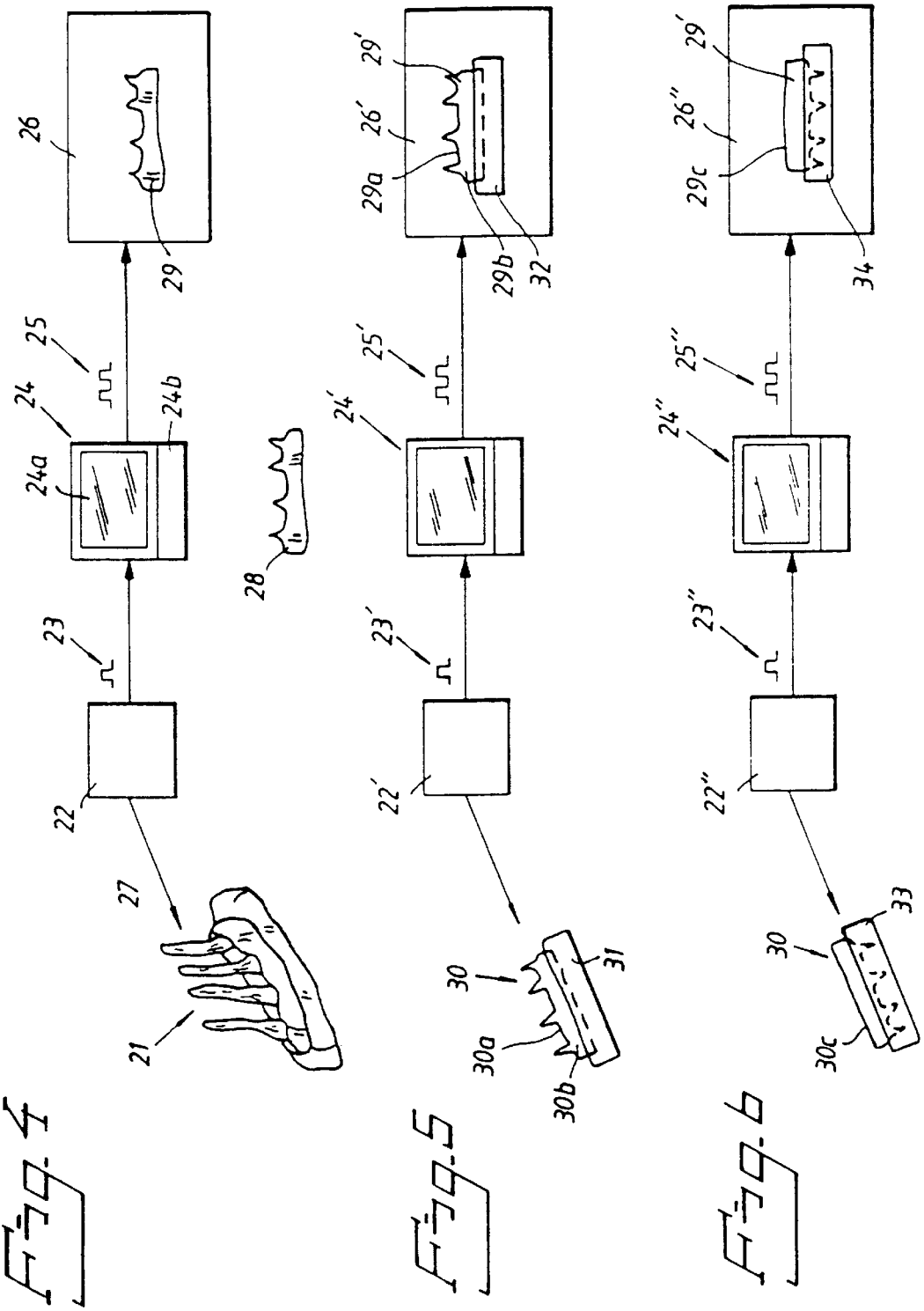

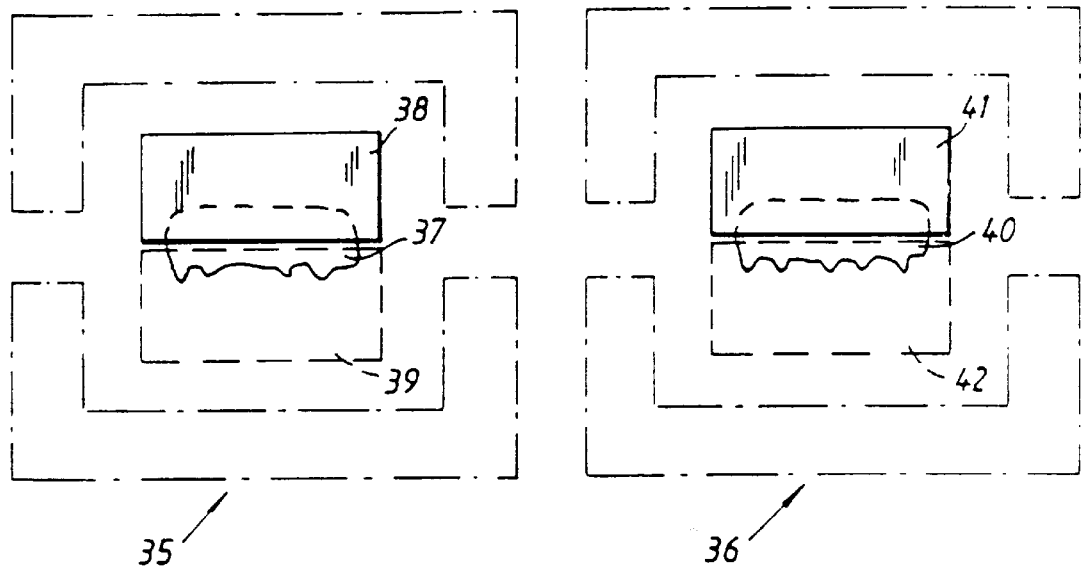
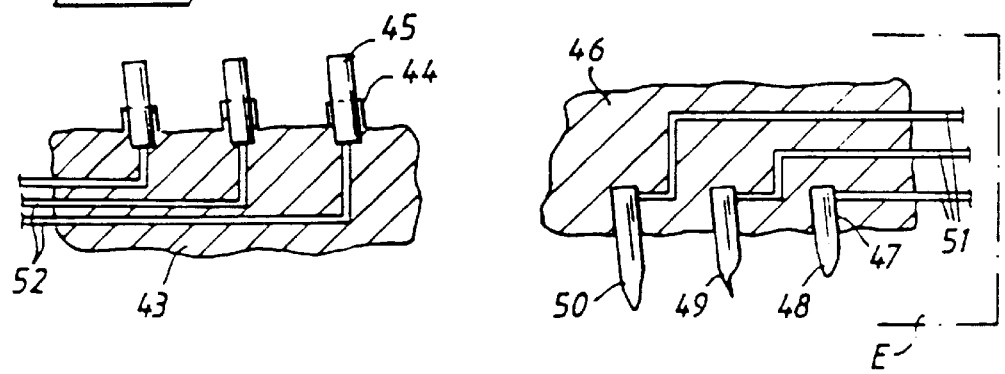
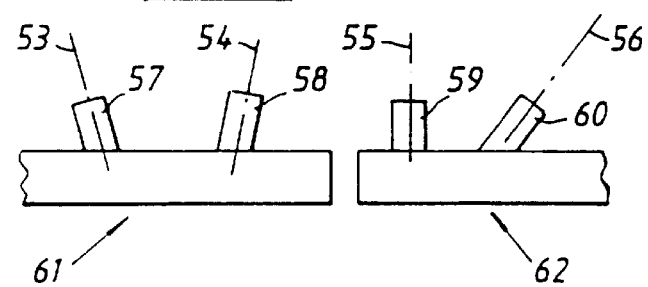

METHOD FOR PRODUCING AN ELONGATE SUPPORTING PART IN A REPLACEMENT CONSTRUCTION, AND SUCH A SUPPORTING PART MANUFACTURED USING THIS METHOD

TECHNICAL FIELD

The present invention relates to a method for producing elongate supporting parts for replacement constructions, for example, in dentures in a human body.

An example of such a supporting part is the "skeleton" of a dental bridge. Each supporting part is intended to be secured in an implant (spacing member thereof) with, as a rule, unique longitudinal axis.

The novel method uses one or more impression models/working models. In each model, the longitudinal courses and connection surfaces of the implants are represented with representation members (dummies). The method also uses a replacement construction model, as well as a surface-reading member, by means of which the shape of the replacement construction model is read, and one or more electrical representations of all, or parts, of the respective shape are generated as a function of the reading. Also included is equipment for producing machining information which preferably comprises computer equipment by means of which one or more items of machining information are generated as a function of the representation(s).

The method also includes the use of one or more electro-erosion devices. The computer equipment (or equivalent) is, in this case, arranged so that it is supplied with each representation obtained from each reading. The computer equipment is also capable of establishing one or more calculations, and/or one or more uses, of the last-mentioned representation or representations in turn to generate one or more second representations which are used as the said machining information items.

The invention also relates to a supporting part for a replacement construction which is intended to be applied in the human body and is in this respect arranged to be anchored in an implant, for example in dentine. The supporting part is furthermore provided with connection members via which securing elements, for example in the form of screws, for anchoring of the replacement construction in the implants which in this case generally have different, unique longitudinal courses.

BACKGROUND OF THE INVENTION

It is already known to manufacture supporting parts, for example for dental bridges, each supporting part, as a finished product, being in the form of a single unit which can be produced from a biocompatible material, for example titanium. Thus, for example, it is known to produce a number of modular elements which are put together to form the unit.

It is also known, when manufacturing dental caps for individual teeth, to use computer technology and mechanical procedures which reduce manufacturing time and permits the high precision which is necessary.

It is also known, in conjunction with the production of dental caps, to use surface-reading members, by means of which outer shapes can be read, and electro-erosion devices for forming recesses in the supporting part itself.

DESCRIPTION OF THE INVENTION

Technical Problem

When manufacturing bridges and replacement constructions, there is a need to be able to use computer aids in combination with improved manufacturing methods which place fewer demands on the experience and training of the personell involved and which improves the manufacturing throughput times. In addition, the manufacturing accuracy must be extremely high so that strict requirements relating to fitting in or on the patient can be satisfied. The invention solves this problem, among others.

The invention also solves the problem of eliminating the use of dental bridges which are made up of modular elements, which have the disadvantage that the longer the supporting part (i.e. the more teeth to be included), the greater the overall error as regards the fit. Thus, by means of the invention, longer replacement constructions can be produced with the prescribed accuracy.

The invention also solves the problem of using conventional scanning and electro-erosion devices in conjunction with the production of dental bridges/elongate supporting elements, even where there are considerable differences in the mutual inclinations between the implants.

SUMMARY OF THE INVENTION

The feature which can principally be regarded as characterizing a method according to the invention is, inter alia, that an original support part is created with the aid of the shape of the replacement construction model, such supporting part original being read completely, or partially, by the surface-reading member to obtain the respective machining information item, and that the respective machining information item is supplied to a machining device for the machining of a blank which is applied in the latter. Before, during, or after the manufacturing stage, an electro-erosion tool is further created by means of the impression model/the working model, which electro-erosion tool is applied in the electro-erosion device and is provided with electro-erosion electrodes at the positions for the representation members, the electrodes being arranged in the same longitudinal directions as the representation members. By means of the electro-erosion device, the blank thus machined is provided with recesses for contact members, by means of which the machined blank designed as a supporting part can be anchored on the implants via the connection surfaces mentioned above. The recesses, and with them the contact members, are in this case assigned longitudinal directions which coincide with the longitudinal axes of the implants or which are slightly displaced in parallel with respect to the longitudinal axes.

The invention is also characterized by the fact that the computer equipment is activated for the initially mentioned calculations and uses to thereby establish for the supporting part an overall outer shape, or partial outer shapes which together form the overall outer shape, which is chosen so that the supporting part is accommodated within the outer shape of the replacement construction. Further characteristics in this respect are that the computer equipment is thereafter activated to give the respective second representation or machining information item which can be related to the overall outer shape of is the supporting part or the respective partial outer shape, and that the respective second representation or machining information item is supplied to a machining device for the machining of a blank which is applied in the latter, which, as a function of the respective supplied second representation or machining information item, gives the blank the established outer shape or respective partial outer shape, with the blank in the last-mentioned case being turned after the respective preceding partial outer shape has been formed. Further characteristics in the last-mentioned case are that before, during, or after the stages in accordance with the above, an electro-erosion tool is created by means of the impression model or the working model which, in this case, is supplemented or provided with electro-erosion electrodes at the positions for the representation members (dummies), the electrodes being arranged in the same longitudinal directions as the representation members. The blank can, in the same way as above, be provided with contact members with the aid of the electro-erosion device.

Embodiments of the methods indicated above can be gleaned, inter alia, from the subclaims which follow.

The feature which can principally be regarded as characterizing a supporting part according to the invention is that the connection members in the supporting part are arranged in electro-eroded recesses which have longitudinal axes coinciding with the longitudinal courses of the contact arrangements, and that the surfaces of the contact arrangements are essentially parallel with respect to the connection surfaces of the implants, and that the longitudinal axes of the contact members and of the implants are coincident or slightly displaced in parallel, always with the necessary high degree of precision as stated above.

The throughput times for manufacturing the replacement construction indicated above can be reduced by more than 50% compared to conventional working methods. In spite of this, it is possible to manufacture dental bridges which have discrepancies of only 50 $\mu$m in the xy axes (+component play), 50 $\mu$m in the z axis and with angle slits of only 50 $\mu$m or less. In this way, it is possible to avoid stresses being built into the patient's dentine, and to prevent the latter from being damaged as a result of such stresses. The invention affords particular advantages in the manufacture of elongate supporting parts by virtue of the fact that the required precision can also be maintained for these parts too.

BRIEF DESCRIPTION OF THE DRAWINGS

Presently proposed embodiments of methods and the supporting part according to the invention will be described hereinbelow with reference to the attached drawings, in which:

FIG. 4 shows, in block diagram form, reading functions, computer processing, and production of a supporting part for a replacement construction, FIG. 5 shows, in block diagram form, the first phase of production of a supporting part, FIG. 6 shows, in block diagram form, a second phase in the production of a supporting part, FIG. 7 shows, in a vertical view, a turning device, FIG. 8 shows, in a vertical view, a turning device for a blank which in the machined form is to constitute the supporting part, FIGS. 9a–9b show the wiring for the electro-erosion function in the working models used, FIG. 10 shows the production of the supporting part in two main parts which can be placed together to form one unit, and where the mutual inclinations of the implants are relatively great.

DETAILED DESCRIPTION OF THE PREFERRED EMBODIMENT

Figure 1:
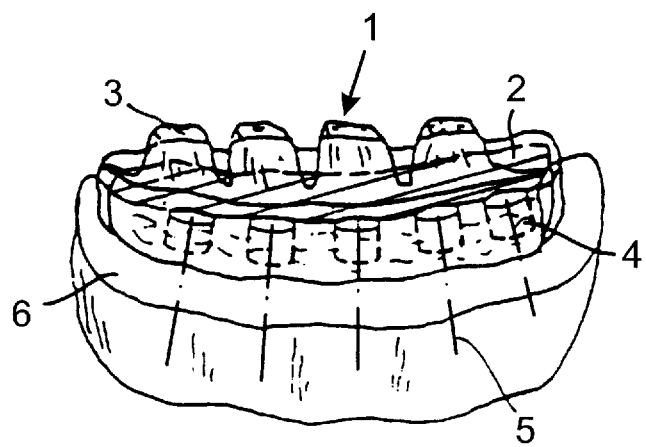
FIG. 1 shows, in perspective view, a replacement construction in the form of a dental bridge.

In FIG. 1, a replacement construction in the form of a dental bridge is shown by 1. The dental bridge includes a supporting part or skeleton 2, and replacement tooth 3 arranged on the latter. The dental bridge is secured in implants 4 which can have different individual inclinations, i.e. their longitudinal axes, 5, have different inclinations. The implants are inserted into the dentine 6 of a human and are provided in a known manner with spacing members.

Figure 2:
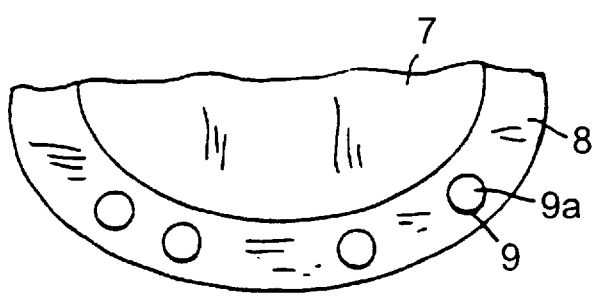
FIG. 2 shows, in horizontal view, an impression model or working model.

In FIG. 2, an impression model or working model which is known per se is indicated by 7. The model is an impression of a patient's mouth, the dentine being shown by 8, and the inserted implants are shown by 9. An implant in this context means both the part which is implanted in the dentine and also the spacing member. The spacing member comprises, in a known manner, contact or connection surfaces 9a.

Figure 3:
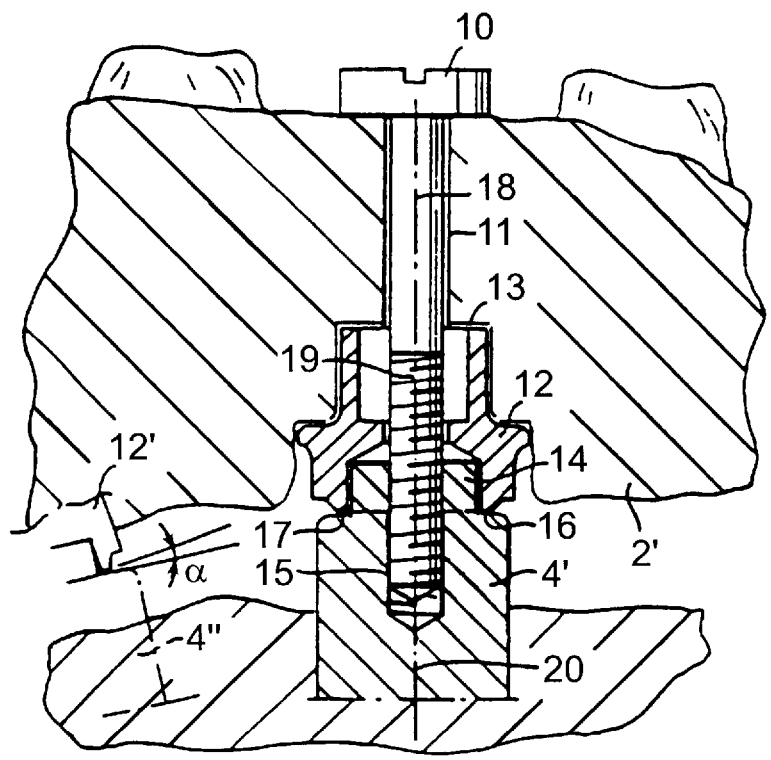
FIG. 3 shows, in a vertical cross-section, the anchoring of the dental bridge in an implant in the dentine.
Figure 11:
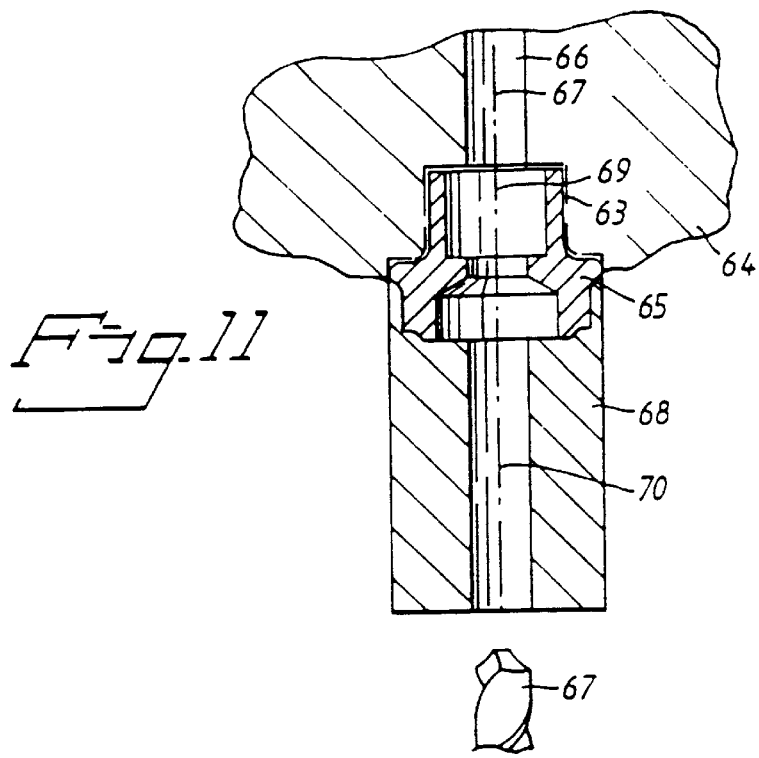
FIG. 11 shows, in a vertical view, hole formation in contact member (bridge part) which has been assigned a position in the supporting part in an electro-eroded recess.

In accordance with FIG. 3, the skeleton part 2' is anchored in the implant 4' with the aid of securing members, for example in the form of a screw 10 which extends through a recess 11 in the skeleton part 2', through a contact member 12 (bridge part) which is anchored in a recess 13 in the skeleton part 2', and further down in a spacer 14 which is provided with an internal thread 15 in which the screw 10 can be tightly screwed. The spacing part of the implant is provided with a contact surface 16 against which the contact surface 17 of the contact part 12 bears. A characteristic aspect of the construction is that the longitudinal axis 18 of the recess 11 coincides with the longitudinal axis 19 of the part 12. The longitudinal axis 20 of the implant can either coincide with the longitudinal axes 18 and 19 or can be slightly displaced in parallel with respect to the longitudinal axes 18 and 19. FIG. 3 also includes a partially shown further implant 4" and parts of a further contact part 12'. Also shown is a slit angle alpha, which is shown in a greatly enlarged form. The slit angle is in fact a maximum of 50 $\mu$m or less.

In FIG. 4, a replacement construction part is shown by 21. This part can be read by means of a surface-reading member 22 which can be of a known type. The surface-reading member generates a first representation 23 as a function of the reading, which representation 23 can be supplied to computer equipment 24, for example, a personal computer. The computer equipment receives and processes the information 23 and generates a second representation or machining information item 25. The latter is transmitted to a machining device 26 which can be a copy-milling machine, numerically controlled machine, etc. The scanning function is represented by an arrow 27, and the surface-scanning member 22 scans the outer shape of the construction part 21 (or a photograph thereof). The digital first representation 23 makes it possible for a picture of the surface-scanned part 21 to be obtained on the screen 24a of the computer equipment. By means of interactive information exchange with the computer 24 via a terminal, the shape of a supporting part 28 can be calculated. In the present case, the said supporting part is able to be accommodated within the outer shape of the construction part 21. By means of known software, in the computer equipment, the supporting part can be made to assume an optimal shape as regards the supporting function in the construction part 21. Machining information which corresponds to the outer shape of the supporting part, and which can consist of the digital machining function 25, is transmitted to the machining device which, as a function of the machining information, machines a blank such that the latter assumes an outer shape 29 corresponding to the supporting part 28.

FIG. 5 shows a reading member 22', computer equipment 24' and a machining device 26' of types corresponding to those in FIG. 4. In this case, a model has been manufactured and has been applied in a holder 31 so that the top side 30a, the outside 30b, and the inside (not seen in the Figure) can be read by means of the surface-scanning member 22'. The representations 23' and 25' are also obtained in this case. The machining device 26' machines a blank 29' which is applied in a holder 32 in the same way as the supporting part 30 is in the holder (+model) 31. The top side of the blank, and its aide surface as shown, are indicated by 29a and 29b, respectively. A shape corresponding to the model 30 is obtained for the blank 29' by machining effected in the machining device 26'. The model 30 can be turned in a turning device which is of a known type. The blank 29' is similarly turned in the same or another device.

In FIG. 6, the model 30 has been turned by means of a holder 33 such that the underside 30c is exposed to the reading member 22". In a corresponding manner, the blank 29' has been turned by means of the holder 34 and exposes its underside 29c for machining. The equipment 22", 24" and 26" can also have a construction similar to that of the corresponding equipment in FIG. 5 or can consist of the same equipment. When the blank has been finished, i.e. when the blank has the shape according to the model 30, the blank is released from the holder 34.

FIGS. 7 and 8 show turning devices 35 and 36, respectively, which are known. In the present case, the model 37 in FIG. 7 is transferred from the holder 38 to the holder 39. The blank 40 is transferred in a corresponding manner from the holder 41 to the holder 42.

In FIG. 9a, an impression model or working model produced from an impression is used as an erosion tool. The model is indicated by 43, and arranged on the model are dummies 44 for the implants and spacing members 45 secured on the implant dummies. The shape of the model can be transferred to a model 46 to obtain recesses 47 in the model 46. Electro-erosion electrodes 48 are arranged in the recesses, which electro-erosion electrodes can be provided with different shapes at their front ends, see 49 and 50. These shapes are dependent on the inclinations of the implants. The electrodes 48 are connected to leads 51 for electric current supply. The model 43 is likewise provided with leads to the spacing members 45 when these are used as electrodes in a final stage of the electro-erosion.

Since the inclinations or the longitudinal axes 53, 54, 55 and 56 of the implants (the dummies) 57, 58, 59 and 60 show considerable variations, problems may arise, during electro-erosion, in obtaining corresponding oblique positions for the contact members (bridge parts) in accordance with what is described below. In this case, the supporting part is manufactured in two parts, which can be related to the parts 61 and 62 in FIG. 10, which two supporting parts are placed together in a final phase of production.

In accordance with the inventive idea, recesses 63 in the supporting part/the skeleton 64 will be formed by electro-erosion using known electro-erosion equipment E. Contact parts or bridge parts 65 will be applied in the recesses. The electro-erosion is carried out in a known manner known by means of the tool parts according to FIGS. 9a and 9b. Carbon bars are used at the start of the electro-erosion, and metal electrodes are used in the final phase in accordance with FIG. 9a. All the recesses in the part 64 are subjected simultaneously to electro-erosion, but compare the case according to FIG. 10. Each recess is provided with a recess 66 for a retention screw according to FIG. 3. The recess 66 is drilled with a drill 67, and use is made of a guide sleeve 68 which is temporarily fastened in the recess 63 by means of adhesive or equivalent, either with or without the contact part 65 applied in the recess 63. The sleeve 68 guides the drill 67 when forming the hole 66 in such a way that the longitudinal axes 67 of the hole 66, 68 of the part 65 and 70 of the sleeve 68 coincide.

Figure 12:
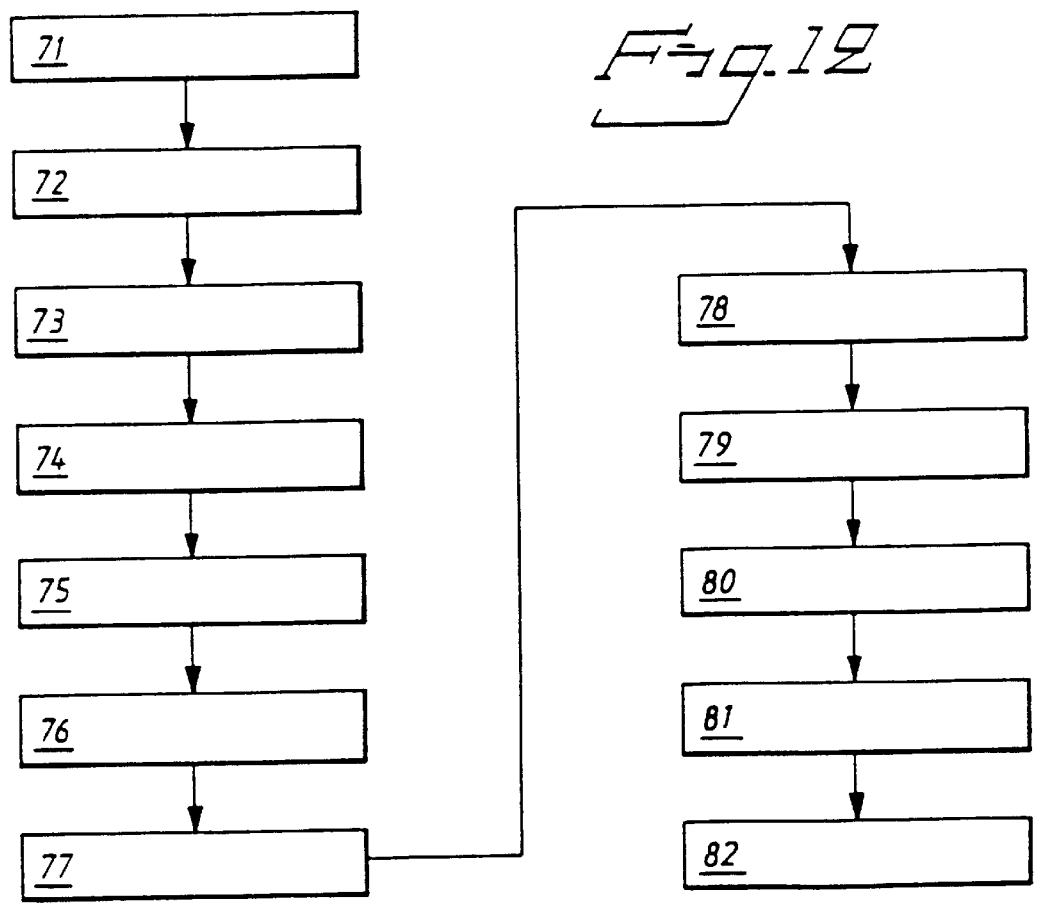
FIG. 12 shows, in flow chart form, examples of the production procedure.

FIG. 12 shows, in the form of a flow diagram, an illustrative embodiment of a method according to the invention. In a first step, an impression 71 of the patient (the mouth) is taken. A model 72 is manufactured from the impression. A wax denture 73 is additionally produced. In the stage 74, the surface of the denture or part of the denture is read. In the stage 75, any correction of the surface to leave room for plastic or porcelain in the finished denture is calculated. Then, in stage 76, any offset surfaces are calculated for machining by milling or corresponding machining equipment. In stage 77, the outside and inside of the blank are machined. The material is then turned in a reference system in accordance with stage 78. The underside of the blank is then machined in a stage 79. Seats for titanium cylinders (contact parts) are thereafter formed by electro-erosion using graphite electrodes mounted on the model in accordance with stage 2. The seats are subjected to electro-erosion, if appropriate, with titanium cylinders mounted directly on the model according to 72. In the next stage 81, the cylinders are mounted and fixed in the bar, which fixing can be effected by laser welding, adhesive or the like. Thereafter, in stage 82, the supporting part thus produced is coated in the traditional way with plastic or porcelain.

In a further embodiment of the inventive concept, the relationship between denture and working model is first recorded with the aid of a silicone insert. Dismantling then takes place tooth by tooth, and the skeleton original is given the shape which the metal skeleton or the supporting part will be given. The skeleton original is screwed tightly on the working model, and the working model is in turn plastered firmly on a 3R holder for reading in accordance with the above. The outside, the top and the inside of the bridge original are read. The 3R holder is then removed and is mounted in a turning device (cf. FIGS. 7 and 8 in accordance with the above). A second 3R holder is mounted on the opposite side in the turning device. An impression in silicone index mounted in the second holder is effected. The holders are removed from the turning device, and a bent titanium blank or equivalent blank is placed in the impression and bonded in place using cyanoacrylate. A further holder which is filled with molten Melotte metal is placed in the turning device. The holder on which the titanium blank is affixed is thereafter placed in the turning device, and the titanium blank is immersed into the molten metal, which is then allowed to cool. The titanium blank or equivalent in this case acquires a position in the same area as the bridge original which has been read. The holder with the titanium blank is transferred to the machining device, for example a copy-milling machine, and machining of the titanium blank takes place in accordance with the bridge original which has been read, cf. above.

A further 3R holder filled with molten Melotte metal is applied in the turning device. The holder with the milled titanium blank is placed on top of the second holder in the turning device and the titanium blank is immersed in the molten metal and is allowed to cool. The holders sit together in this case, and it is possible to take them out of the turning device and release the upper holder by heating with a flame in such a way that the titanium blank is turned up and down in the lower holder, ready for machining of the underside of the bridge. It is possible here for the underside of the bridge original to be read. The holder in which the working model with the bridge original is plastered firmly and introduced into the turning device, and a new holder is placed in the opposite direction in the turning device. Silicone is applied, and the holders are brought together, so that an impression of the bridge original is obtained.

The holders are removed from the turning device, and the bridge original unscrewed and is pressed into the impression in the second holder so that the underside is clearly exposed for reading. The underside of the titanium blank can be copied in the machining device according to the above, and the finished titanium blank is ready to be subjected to electro-erosion to produce the seats for the contact parts or the bridge parts. Impression spacers are mounted on the spacing members on the plastered-on working model, and an impression can then be taken of the bridge parts.

A 3R holder is mounted on the opposite side in the turning device, and plastering is carried out in such a way that the holders are held together when taken out of the turning device. The holder with the impression is removed, and carbon electrodes in accordance with the above are placed in impressions of the bridge parts. A further plaster model is produced, in which case the ends of the carbon electrodes are not covered: instead, holes for the connection of electric leads are present once the plaster has hardened. The model can thereafter be plastered firmly in an opposite holder in which the leads are combined to form a tuft.

Once the plaster has hardened, the current is applied, and recesses are formed by spark machining in the upwardly and downwardly turned titanium blank. The holder with the carbon electrodes is thereafter taken down, and the holder with the master model with affixed titanium bridge parts is set up for spark machining. Spark machining with titanium against titanium uses less current than in the case with a carbon electrode. The electro-erosion continues until the contact part or the bridge part is in place in the bridge original, i.e. so that its flange is immersed in the material.

The holder with the bridge blank is thereafter dismantled, and the holes in accordance with the above are drilled for guide pins in the same direction in which the bridge part is pointing. The bridge blank is then removed and the bridge part is bonded after cleaning on the dismantled master model. The bridge blank is unscrewed from the master model and welded at points with laser positions, for example four positions.

Each bridge part is secured in this manner. The fit is tested on the master model, and if the result is acceptable, the bridge parts are definitively welded all around. The bridge blank can thereafter be polished and can be provided with attachments for the teeth. If the bridge is intended for porcelain firing, it will be finished for such.

The above method is varied depending on whether porcelain firing is to be carried out. The relationship between denture and the working model is established with the aid of an internal and an external silicone index. Dismantling tooth by tooth is thereafter carried out, and at the same time most of the pink wax is removed. The silicone index is put back and a hole is formed on the top for filling-in of modelling wax. In the latter, wax is poured into the cavity and the wax is then allowed to cool. When the index is removed, the teeth are shown in wax. Scale of the teeth 1.5 mm in order to create space for the porcelain and also to give the design which is expedient for this particular bridge.

It is possible for the supporting part or skeleton produced to be designed for all clinical implant cases, i.e. both the whole of the upper jaws and lower jaws and also partial cases. The skeleton satisfies the design requirements which are set by ethics and function irrespective of whether acrylic, composite or porcelain is used. The mucous membrane contact can be made of titanium if so desired. The production time for the finished skeleton exceeds 4 hours. The skeleton has machined connections to the spacer. The surface is machined and is free from build-up of loose titanium chips and have a strength corresponding to the strength in previously known methods. It is possible for the cross-section to be 0.07 mm for all clinical cases.

The invention is not limited to the embodiment shown above by way of example, and instead can be modified within the scope of the following patent claims and the inventive concept.

We claim:

1. A method for producing an elongate supporting part for a replacement construction in a human body and intended to be secured in implants with unique longitudinal courses, and using at least one working model in which said longitudinal courses and connection surfaces of said implants are represented by representation members, said method comprising the steps of:

reading an outer shape of said working model with a surface reading member to generate an electrical representation of said outer shape;

supplying computer equipment with said electrical representation;

performing calculations in said computer equipment to establish a shape for said supporting part, whereby said supporting part is accommodated within said outer shape of said replacement construction;

generating machining information with said computer means which represents said shape of said supporting part;

providing said machining information to a machining device;

machining a blank with said machining device such that said blank obtains said shape;

creating an electro-erosion tool by providing electro-erosion electrodes in said working model at positions for said representation members and arranging said electrodes in the same longitudinal direction as said representation members; and creating a recess in said blank with said electro-erosion tool for contact members, whereby said blank can be anchored on said implants via connection surfaces on said contact members, said recess and said contact members have longitudinal axes which coincide with axes of said implants.

2. The method of claim 1 further comprising the steps of:

creating a supporting part original with the aid of said replacement construction;

obtaining said electrical representation by reading said supporting part original;

obtaining said machining information based on said electrical representation;

machining a blank based on said machining information;

creating an electro-erosion tool by providing electro-erosion electrodes in said working model at positions for said representation members and arranging said electrodes in a same longitudinal direction as said representation members; and creating a recess in said blank with said electro-erosion tool for contact members, whereby said blank can be anchored on said implants via connection surfaces, said recess and said contact members have longitudinal axes which coincide with axes of said implants.

3. A method according to claim 2 further comprising the steps of:

securing said supporting part original on said working model;

securing said working model in a first holder; and scanning an outside, top, and inside of said supporting part original.

4. A method according to claim 3 further comprising the steps of:

securing said first holder and a second holder on opposite sides of a turning device;

placing impression compound in said second holder;

activating said turning device to make an impression of said supporting part original in said impression compound; and placing said blank in said impression, the external dimensions of said blank exceeding the dimensions of said impression.

5. A method according to claim 4 further comprising the steps of:

placing a third holder in said turning device with said second holder;

filling said third holder with a molten metal;

activating said turning device to immerse said blank in said molten metal; and cooling said molten metal whereby said blank obtains the same position as said original in said third holder.

6. A method according to claim 5 further comprising the steps of:

machining said blank in said third holder to correspond with said machining information obtained from said supporting part original.

7. A method according to claim 6 further comprising the steps of:

placing a fourth holder in said turning device with said third holder, said third holder holding said blank;

filling a fourth holder with molten metal;

activating said turning device to immerse an upper part of said third holder in said molten metal;

cooling said molten metal; and removing said third holder by heating it to expose an underside of said blank.

8. A method according to claim 7 further comprising the steps of:

placing said working model in a fifth holder;

filling a sixth holder with impression compound;

arranging both said fifth and sixth holders in said turning device;

activating said turning device to create an impression of said supporting part original in said impression compound;

removing said model from said fifth holder and securing said model in said sixth holder in order to expose an underside of said supporting part original;

reading said underside with said surface reading member to create said electrical representation;

generating said machining information from said electrical information with said computer means; and machining said underside of said blank in accordance with said machining information.

9. A method according to claim 2 further comprising the steps of:

mounting impression spacers on said representation members on said working model;

taking an impression of said working model with a seventh holder;

placing electrodes in recesses of said impression created by said representation members;

taking a plaster model of said model of said preceding step allowing access for leads to be connected to said electrodes;

placing said plaster model in an eight holder opposite said seventh holder, holding said blank, in said turning device;

subjecting said recesses to electro-erosion from an underside of said blank to create eroded recesses;

removing said eighth holder and replacing it with said working model;

performing electro-erosion until said contact part is in place in said supporting part original;

providing through-holes in said blank which extend in the same longitudinal direction as said eroded recess; and securing said contact member in said blank.

10. A method according to claim 9 further comprising the steps of:

arranging guide sleeves in said eroded recess to guide drilling of said through-holes.

11. A method according to claim 1 wherein said computer equipment determines several partial shapes which together form said outer shape and said blank is turned in said machining device after one of said partial shapes has been formed in order that another partial shape may be formed.

* * * * *